(12) United States Patent  (10) Patent No.: US 8,509,885 B2
Snyder et al.  (45) Date of Patent: *Aug. 13, 2013

(54) S AND M FOR ANALYZING AND ASSESSING DEPRESSION AND OTHER MOOD DISORDERS USING ELECTOENCEPHALOGRAHIC (EEG) MEASUREMENTS

(71) Applicant: NEBA Health, LLC, Augusta, GA (US)

(72) Inventors: Steven M. Snyder, Boulder, CO (US); James D. Falk, Duluth, MN (US)

(73) Assignee: Neba Health LLC, Augusta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/627,382

(22) Filed: Sep. 26, 2012

(65) Prior Publication Data
US 2013/0023783 A1 Jan. 24, 2013

Related U.S. Application Data

(63) Continuation of application No. 11/565,305, filed on Nov. 30, 2006, now Pat. No. 8,311,622.

(51) Int. Cl.
A61B 5/0476 (2006.01)

(52) U.S. Cl.
USPC ............................................. 600/544

(58) Field of Classification Search
USPC .................................. 600/544, 545
See application file for complete search history.

(56) References Cited

U.S. PATENT DOCUMENTS 8,311,622 B2 * 11/2012 Snyder et al. ................. 600/544

OTHER PUBLICATIONS

Blackhart et al. "Can EEG Asymmetry Patterns Predict Future Development of Anxiety and Depression? A Preliminary Study." Biological Psychology 72 (2006) 46-50.*
Stassen et al. "Genetic Determination of the Human EEG." Hum Genet (1988) 80: 165-176.*

* cited by examiner

*Primary Examiner* — Patricia Mallari
*Assistant Examiner* — Meredith Weare
(74) *Attorney, Agent, or Firm* — Duft Bornsen & Fettig LLP

(57) ABSTRACT

This invention is directed to systems and methods for analyzing depression, and more particularly relates to systems and methods for analyzing and assessing depression and mood disorders in an individual using electroencephalographic measurements. Embodiments of the invention are not limited to depression, but can also include other mood disorders such as bipolar disorder and other disorders with at least one genetic-related component.

6 Claims, 7 Drawing Sheets

S AND M FOR ANALYZING AND ASSESSING DEPRESSION AND OTHER MOOD DISORDERS USING ELECTOENCEPHALOGRAHIC (EEG) MEASUREMENTS

RELATED APPLICATION

This application is a continuation application of U.S. patent application Ser. No. 11/565,305, entitled "Systems and Methods for Analyzing and Assessing Depression and Other Mood Disorders Using Electroencephalographic (EEG) Measurements" filed Nov. 30, 2006 which claims priority to U.S. Provisional Ser. No. 60/741,843, entitled "Systems and Methods for Analyzing and Diagnosing Depression Using Electroencephalographic (EEG) Measurements", filed Dec. 1, 2005, both are incorporated herein by reference.

FIELD OF THE INVENTION

This invention is directed to systems and methods for analyzing depression, and in particular relates to systems and methods for analyzing and assessing depression and other mood disorders in an individual using electroencephalographic measurements.

BACKGROUND OF THE INVENTION

According to United States Health and Human Services (USHHS) 2002 Report on Mental Health in the United States, approximately 3.7% of children 5-17 years old will be diagnosed with depression in a given year. That means approximately 2.2 million annually for a child/adolescent market of US$440 million if averaging 1 scan per patient. According to the National Institute for Mental Health (NIMH), every year 9.5% of the population suffers one or more depressive disorders, with women experiencing depression about twice as often as men. In the United States, this means about 28.1 million annually for a general population market worth about US$5.62 billion if averaging 1 scan per patient. While diagnosis may only require one scan, tracking of treatment may require multiple scans.

Quantitative electroencephalography (qEEG) has been utilized by some healthcare professionals to analyze and diagnose certain psychopathological conditions. For instance, literature has reported nearly 100 studies which have examined qEEG in association with emotions and related psychopathology (See Allen & Kline, 2004; Coan & Allen, 2004). In some of these studies, asymmetry between left and right frontal qEEG measurements has been observed to be associated with individuals either demonstrating or being at risk for depressive psychopathology. One analysis of qEEG measurements for asymmetry can be performed utilizing a Fast Fourier Transform (FFT) that can provide averaged results for all epochs accepted after artifacting. At least two studies have observed greater statistical differences between experimental groups by using an analysis that includes FFT of each individual epoch and then determination of a percentage time with left or right favored asymmetry (See Baehr, Rosenfeld, Baehr, & Earnest, 1998; Baehr, Rosenfeld, Miller, & Baehr, 2004).

Quantitative electroencephalography (qEEG) has also been used by other healthcare professionals or personnel for other types of monitoring, such as monitoring the effects of anesthesia on a patient. For example, analysis of qEEG measurements using discriminant analysis can provide a discriminant variable called "cordance." This type of analysis can also be used for investigating brain lesions and characterizing patients with dementia.

Frontal alpha qEEG asymmetry has been commonly used by healthcare professionals and researchers to investigate depressive disorders. Conventional techniques utilizing calculation of asymmetry, such as simple arithmetic difference between the power values of the two hemispheres, to identify depression have been used by healthcare professionals. One technique, such as neurofeedback, biofeedback or neurotherapy, uses qEEG asymmetry as a marker variable to treat depression. This technique uses simple subtraction of left and right hemisphere power variables. Other similar techniques examine an arithmetic difference between power values of the frontal regions of the left and right hemispheres determined using an FFT of all included epochs averaged in combined sets. There can be substantial variability in the power at the frontal sites of each hemisphere. With prior techniques, valuable information from the variability can be lost in the averaging process, and valuable information from the averaged values can be diminished when not accounting for the variability. Meta-analysis of various literature using such conventional techniques can produce an effect size of approximately 0.6, which estimates a classification accuracy of about 60%. That is, identification and diagnosis of depression using such conventional techniques can be approximately 60% accurate.

One conventional technique uses a discriminant analysis and a cluster analysis to diagnose depression. This technique can require discriminant analysis of specific qEEG variables including those of absolute power, relative power, coherence, and asymmetry. However, this technique can also utilize the qEEG variables in the manner typical for the field as described above, which can lose valuable information from the variability.

Single recordings of qEEG measurements can be utilized to analyze or investigate asymmetry. Some studies have utilized a repeated measures design coupled with a relatively simple method for isolating relatively stable qEEG components. This static-type method involves a basic averaging technique with the repeated measures, and can lead to improved precision in the investigation and analysis of asymmetrical qEEG measurements and results. See (Davidson, 1998).

One mathematical technique can separate qEEG measurements into respective static components and dynamic components. Prior applications of this technique have been limited to studies of qEEG and genetics, which demonstrated the effectiveness of this type of analysis in determining the stable, genetic components of qEEG. When using this technique in studies of dizygotic and monozygotic twins as well as immediate family members and the general population, genetic similarity between individuals has been associated with the spectral pattern similarity of the stable components of the qEEG data (Stassen, Lykken, Propping, & Bomben, 1988).

Therefore, a need exists for systems and methods for analyzing and assessing depression in an individual using electroencephalographic measurements. Another need exists for systems and methods for analyzing and assessing mood disorders in an individual using electroencephalographic measurements.

Yet another need exists for systems and method for analyzing and assessing bipolar disorder in an individual using electroencephalographic measurements.

Yet another need exists for systems and method for analyzing and assessing a disorder with at least one genetic-related component in an individual using electroencephalographic measurements.

SUMMARY OF THE INVENTION

Systems and processes according to various aspects and embodiments according to the invention address some or all of these issues and combinations of them. They do so by providing at least one system and method for analyzing and assessing depression in an individual using electroencephalographic measurements. Embodiments of the invention are not limited to depression, but can also include other mood disorders such as bipolar disorder, and other disorders with at least one genetic-related component.

Embodiments of the invention can incorporate multiple methods for accounting for the variability of individual qEEG data sets. Embodiments of the invention can also incorporate multiple methods for capturing information associated with the variability of individual EEG data sets, which can be estimated by meta-analytic methods to be of significant value when applying EEG to assessment of mood disorders. Embodiments of the invention can retain relatively important information from the variability of the EEG data that may be otherwise lost, discarded, or not used by conventional techniques. Asymmetry values can be derived from the static and dynamic qEEG components. For example, static components ("static spectral asymmetry") can be applied to assessment of depressive individuals. Asymmetry values derived from the dynamic components ("dynamic spectral asymmetry") can be applied to the tracking of changes in symptomology over time in depressive individuals in the presence and absence of treatment. Conventional techniques do not distinguish or otherwise separate the static and dynamic components of qEEG. Using meta-analytic extrapolation, it is estimated that embodiments of the invention can generate an effect size of about 2.6 for a classification accuracy of approximately 90%. While the approximate 60% accuracy of prior conventional techniques may not be sufficient for use in clinical applications, the approximately 90% accuracy of some embodiments of the invention can meet diagnostic standards.

One embodiment of the invention is a process that includes collecting repeated baseline qEEG measures, and analyzing single epochs of asymmetry from static and dynamic qEEG components based at least in part on a spectral pattern mathematical technique. Spectral patterns can be obtained for each electrode site from the qEEG data sets by artifact removal, subdivision of epochs, and performance of Fast Fourier Transforms on individual epochs. From each set of spectra, variability plots can be created in which each set of range and frequency points can define a feature vector of the spectral pattern. In one example, a static component of the qEEG data can be calculated as the intersection of the set of spectral patterns for each electrode. In another example, the dynamic component for a particular single spectral pattern can be determined as the remainder of the spectral pattern after the overall static component has been removed.

The asymmetry values derived from the static components can be applied to assessment of individuals with depressive and other related emotional psychopathology. The asymmetry values derived from the dynamic components can be applied to the tracking of changes in symptomology over time with individuals in the presence and absence of treatment.

Embodiments of systems, methods, and apparatus in accordance with the invention can perform some or all of the following functionality: (1) repeated qEEG measurements and analysis, (2) FFT analysis of individual epochs, (3) separation of static and dynamic qEEG components, (4) calculation of static and dynamic asymmetry variables based in part on at least spectral pattern analysis, and (5) application of static and dynamic variables to disorder risk and disorder tracking, respectively. For example, in one embodiment, a combination of the above functionality and techniques can be used to analyze and diagnose depression in a patient.

One embodiment of the invention includes a method for analyzing and assessing a mood disorder in a person. The method includes receiving a plurality of electroencephalography data associated with the person. Furthermore, the method includes determining at least one static component of a portion of the plurality of electroencephalography data. Moreover, the method includes determining static asymmetry in the static component of the portion of the plurality of electroencephalography data. Further, the method includes based at least in part on the static asymmetry in the static component of the portions of plurality of electroencephalography data, determining an indication for whether the person is at risk for the mood disorder.

In one aspect of an embodiment of the invention, the method can include determining at least one dynamic component of a portion of the plurality of electroencephalography data. The method can also include determining dynamic asymmetry in the dynamic component of the portion of the plurality of electroencephalography data. In addition, the method can also include based at least in part on the dynamic asymmetry in the dynamic component of the portions of the electroencephalography data, determining an indication for predicting and evaluating a treatment response of the mood disorder.

In another aspect of an embodiment of the invention, the method can include wherein determining at least one static component of the portion of the plurality of electroencephalography data comprises determining a static spectral pattern.

In yet another aspect of an embodiment of the invention, the method can include wherein determining dynamic asymmetry in the dynamic component of the portion of the plurality of the electroencephalography data comprises determining a dynamic spectral pattern.

In a further aspect of an embodiment of the invention, the method can include wherein determining static asymmetry in the static component of the portion of the plurality of the electroencephalography data comprises removing the intersection of a left and right spectral pattern from an original left and right static spectral pattern.

In yet another aspect of an embodiment of the invention, the method can include wherein determining dynamic asymmetry in the dynamic component of the portion of the plurality of the electroencephalography data comprises removing the intersection of a left and right dynamic spectral pattern from an original left and right dynamic spectral pattern.

In another aspect of an embodiment of the invention, the method can include wherein determining static asymmetry in the static component of the portion of the plurality of the electroencephalography data can further comprise determining an average of maximum and minimum powers of a right and left side static component.

In another aspect of an embodiment of the invention, the method can include wherein determining dynamic asymmetry in the dynamic component of the electroencephalography data can further comprise determining an average of maximum and minimum powers of a right and left side dynamic component.

In yet another aspect of an embodiment of the invention, the method can include wherein the mood disorder comprises at least one of the following: depression, bipolar disorder, or a disorder with at least one genetic-related component.

Another embodiment includes a method for analyzing and assessing a mood disorder in person using electroencephalography data. The method includes collecting electroencephalography data from the person. In addition, the method includes determining a static component associated with at least some of the electroencephalography data. Furthermore, the method includes determining a dynamic component associated with at least some of the electroencephalography data. Moreover, the method includes determining asymmetry in either the static or the dynamic component. Further, the method includes based at least in part on either the asymmetry in the static component or the dynamic component, evaluating a characteristic associated with the mood disorder.

In one aspect of an embodiment of the invention, the method can include determining a left side spectral pattern. In addition, the method can include based at least in part on the electroencephalography data, determining a right side spectral pattern. Furthermore, the method can include removing an intersecting portion of the left side spectral pattern and right side spectral pattern to obtain an overall asymmetric spectral pattern.

In another aspect of an embodiment of the invention, the method can include wherein determining asymmetry in either the static or the dynamic component further comprises valuating a ratio of the intersecting portion of the left side spectral pattern and right side spectral pattern with a union of the left side spectral pattern and right side spectral pattern.

In yet another aspect of an embodiment of the invention, the method can include wherein determining asymmetry in either the static or the dynamic component comprises implementing a learning-type algorithm to define one or more weighting factors to ascertain a similarity of each frequency band associated with the electroencephalography data.

In yet another aspect of an embodiment of the invention, the method can include wherein determining asymmetry in either the static or the dynamic component comprises determining a percent of time the patient's left side is favored or disfavored relative to the patient's right side; and comparing the percent of time the patient's left side is favored or disfavored relative to the patient's right side.

In another aspect of an embodiment of the invention, the method can include wherein determining asymmetry in either the static or the dynamic component comprises using at least one vector to derive a respective power for each frontal region; and comparing the respective powers for each frontal region.

In a further aspect of an embodiment of the invention, the method can include wherein the characteristic can comprise at least one of the following: a risk of having the mood disorder, or a symptom of the mood disorder.

Another embodiment of the invention includes a method for analyzing and assessing a mood disorder in person using electroencephalography data. The method includes collecting electroencephalography data from the person. In addition, the method includes determining a static component associated with at least some of the electroencephalography data. Furthermore, the method includes determining asymmetry in the static component. Moreover, the method includes based at least in part on the asymmetry in the static component, evaluating a characteristic associated with the mood disorder.

Yet another embodiment of the invention includes a method for analyzing and assessing a mood disorder in person using electroencephalography data. The method includes collecting electroencephalography data from the person. In addition, the method includes determining a dynamic component associated with at least some of the electroencephalography data. Furthermore, the method includes determining asymmetry in the dynamic component. In addition, the method includes based at least in part on the asymmetry in the dynamic component, evaluating a characteristic associated with the mood disorder.

Yet another embodiment of the invention includes a system for analyzing and assessing a mood disorder in a person. The system includes a data collection module and a report generation module. The data collection module is adapted to receive a plurality of electroencephalography data associated with the person. The report generation module is adapted to determine at least one static component of a portion of the plurality of electroencephalography data, and further adapted to determine static asymmetry in the static component of the portion of the plurality of electroencephalography data. The report generation module is further adapted to output an indication of whether the person is at risk for the mood disorder based at least in part on the static asymmetry in the static component of the portions of plurality of electroencephalography data.

In yet another aspect of an embodiment of the invention, the system can include wherein the report generation module is further adapted to determine at least one dynamic component of a portion of the plurality of electroencephalography data. The report generation module can be further adapted to determine dynamic asymmetry in the dynamic component of the portion of the plurality of electroencephalography data. In addition, the report generation module can be further adapted to output an indication of predicting a treatment response of the mood disorder based at least in part on the dynamic asymmetry in the dynamic component of the portions of the electroencephalography data. Furthermore, the report generation module can be further adapted to output an indication of evaluating a treatment of the mood disorder based at least in part on the dynamic asymmetry in the dynamic component of the portions of the electroencephalography data.

Therefore various systems and processes according to various embodiments of the invention can include:

(1) Systems and methods for analyzing and assessing depression in an individual using electroencephalographic measurements;

(2) Systems and methods for analyzing and assessing mood disorders in an individual using electroencephalographic measurements;

(3) Systems and methods for analyzing and assessing bipolar disorder in an individual using electroencephalographic measurements;

(4) Systems and methods for analyzing and assessing a disorder with at least one genetic-related component in an individual using electroencephalographic measurements;

(5) Systems and methods for providing an improved, quantitative, and non-invasive method for assessing both the state and trait presence of emotional psychopathologies using qEEG procedures;

(6) Systems and methods for providing a qEEG procedure enabling practitioners to test for emotional psychopathologies using a non-biased, accurate method; and (7) Systems and methods for providing a qEEG procedure enabling practitioners to predict and track therapy response, medication response, and time course of emotional psychopathologies using a non-biased, accurate method.

Other systems and processes according to various embodiments of the invention will become apparent with respect to the remainder of this document.

DETAILED DESCRIPTION

Figure 1:
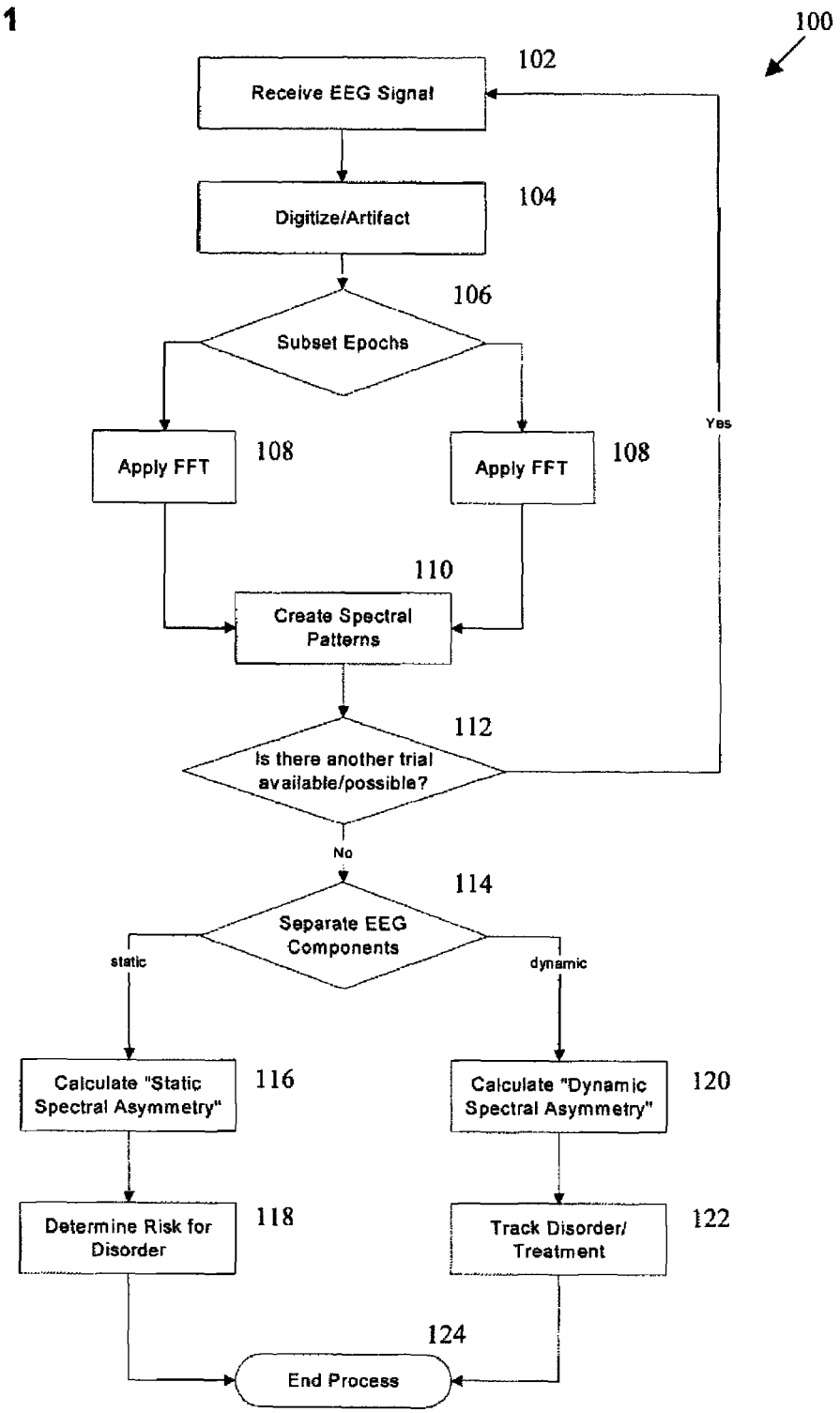
FIG. 1 is a flowchart for an example method in accordance with an embodiment of the invention.

The invention relates to systems and processes for analyzing and assessing depression in an individual using electroencephalographic measurements. One embodiment of the invention relates to systems and processes for analyzing and assessing depression. Another embodiment relates to systems and processes for analyzing and assessing mood disorders. Yet another embodiment relates to systems and processes for analyzing and assessing bipolar disorder. Yet another embodiment relates to systems and processes for analyzing and assessing a disorder with at least one genetic-related component.

Before describing the drawings and examples of embodiments in more detail, several terms are described below in an effort to clarify the terminology used in this document. Additional and fuller understanding of these terms will be clear upon reading this entire document:

"QEEG DATA": Any data collected from a patient using devices, or processes including, but not limited to, electroencephalography (EEG), and the like.

"INDICATOR": A characteristic that identifies a particular aspect of a healthy or pathological condition. An indicator, also known as an "indicator variable," provides, or otherwise can be combined with research or other data to provide, context to a biological measurement and facilitates interpretation of the biological measurement with respect to a particular condition. Typically, an indicator is researched, verified, and tested to be a generally reliable, repeatable, or statistically significant characteristic for a particular aspect of a condition.

"HEALTH CONDITION": A physical or mental condition of a patient including, but not limited to, healthy or less than healthy conditions, chronic or acute conditions comprising healthy or less than healthy conditions, one or more disorders, complexes, diseases, infections, birth defects, accident sequella, or pathologically-related problems or afflictions.

"EPOCH": An arbitrary unit or amount of data in a raw data file, such as an electrophysiological data file, collected over a period of time. A raw data file can be decomposed into a series of epochs. Each epoch can contain information relating to raw biological activity, such as raw electrophysiological multichannel activity, of any number of channels over any period of time.

"ARTIFACT": Some or all signals or activity in a raw data file, such as a raw electrophysiological data file, which can be considered by experts or others skilled in the art to be due to the movement of some part of a particular patient, a subject's body, and/or of any environmental origin associated with a patient or subject. Contributors to an artifact can include, but are not limited to, heart electrical activity (EKG), eye movement (FOG), muscle tension (EMG), and respiration. In some embodiments, artifacts can frequently overlap other physiological signals of interest in either or both the time and frequency domains.

"ARTIFACTING": A process or method that can be performed by a human, or a set of computer-executable instructions such as a computer program, that involves scanning some or all portions of a particular epoch containing an artifact, and if an artifact exists, can mark some or all portions of any particular epoch accordingly as "included" or "deleted."

Embodiments of the invention can be based on the recognition that individuals with depression, a mood disorder, or other disorder with at least one genetic-related component typically have a baseline level of behavioral functioning with an intermittent, acute level of behavioral expression superimposed over the top of the baseline. Embodiments of the invention can also be based on the recognition that qEEG data or measurements can be separated into a baseline set of information with acute qEEG features superimposed over the top of the baseline, in other words, static (baseline) and dynamic (superimposed) components of qEEG data or measurements.

Embodiments of the invention can separate the static and dynamic components of a patient's qEEG data or measurements, and apply the static component to identify a baseline presence of a particular disorder or the risk for a particular disorder. Embodiments of the invention can use the dynamic qEEG component to track acute levels of behavioral expressions of the patient over time, which can have applications to, for instance, medication response, therapy response, and time course of a particular disorder.

In one embodiment, at least two sessions of qEEG data measurements can be obtained from a single patient or subject, which in some instances, translates to more than one clinical visit for the patient or subject. In some embodiments, suitable qEEG data measurements can be obtained in one clinical visit with one session of qEEG data measurements from the patient or subject. In such embodiments, it may be possible that with a large enough data set from a single session, the variability of the qEEG data measurements can be determined using spectral pattern techniques described herein. In some instances, the suitability of use of qEEG data measurements from a single session can be verified with the collection and analysis of repeated measures validation data in a clinical study.

Embodiments of the invention can measure or otherwise determine asymmetry in a set of qEEG data measurements. Asymmetry can be defined as a difference between two sets of data measurements. Asymmetry can be measured or otherwise determined using some or all of the following methods:

In one method, spectral asymmetry can be calculated from a set of left and right electrode spectral patterns. For example, the intersecting data from a left electrode spectral pattern and a right electrode spectral pattern can be removed from each original pattern. The remaining data from each pattern yields the spectral asymmetry between the two sets of data or patterns. Analysis of similarity between spectral patterns can be performed using a ratio of the intersection of the sets and the union of the sets. In one embodiment, overall similarity can be calculated using a learning-type optimization algorithm or another similar technique to define one or more weighting factors in the summation of the contribution to similarity of each frequency band.

In another method, feature vectors can be used in the derivation of standard frontal power and asymmetry qEEG values of the static and the dynamic components in the alpha frequency range.

In yet another method, percent time of left and right favored asymmetry can be calculated using the static and dynamic qEEG components separately.

Using some or all of the methods associated with determining asymmetry, asymmetry values derived from the static components ("static spectral asymmetry") can be applied to the assessment and diagnosis of depressive individuals. The asymmetry values derived from the dynamic components ("dynamic spectral asymmetry") can be applied to the prediction and tracking of changes in symptomology over time in depressive individuals in the presence and absence of treatment.

One example of a method for analyzing and assessing depression in an individual using qEEG measurements is described in FIG. 1. The example method 100 is not limited to depression, but can also include other mood disorders such as bipolar disorder and other disorders with at least one genetic-related component. The example method 100 can be performed by a system such as 602 in FIG. 6.

The method 100 shown in FIG. 1 begins at block 102. In block 102, an EEG signal associated with a subject or patient is received. That is, qEEG data measurements associated with a subject or patient are received by a system, such as 602 in FIG. 6. For example, a plurality of electrode sites can be located with respect to a patient's body, such as the patient's head, using a qEEG data collection device, system, or technique and the International 10-20 system of electrode placement. A suitable system associated with electrodes capable of collecting qEEG data measurements is described below with respect to FIG. 6. The areas on the patient's body, for instance, the patient's head, can be cleaned using an appropriate qEEG preparation cleaner and alcohol. For example, a patient can be fitted with a stretch Lycra™ cap that can be adjusted so that the proper electrodes sit over the sites located in the step above. Once the electrode cap is properly placed, a syringe can be used to apply conductive gel to the patient's scalp in the selected sites. Each electrode site can then be checked by a healthcare professional or personnel to ensure that an accurate qEEG data measurement can be obtained from that site.

In one embodiment, qEEG measurements can be collected both with the subject's eyes closed and with the subject's eyes opened. For example, qEEG measurements can be collected for approximately 20 minutes with a subject's eyes closed (approximately 630 epochs) and for approximately 10 minutes with the subject's eyes opened data (approximately 315 epochs).

Block 102 is followed by block 104, in which the qEEG data is digitized and screened for artifacts. In one embodiment, the qEEG data can be digitized and screened by a system, such as 602 in FIG. 6, and the qEEG data can be analyzed to identify artifacts. In one example, affected epochs of qEEG data can be removed from a particular data set of interest. In another embodiment, at least 15 epochs of data, which may be minimally affected by artifacts, can be collected from a particular subject with the subject's eyes closed and with the subject's eyes open. In another embodiment, at least 45 epochs of data can be collected from a particular subject with the subject's eyes closed.

Block 104 is followed by block 106, in which epoch subsets are processed. For example, once a sufficient number of relatively artifact-free qEEG data epochs are obtained from a particular patient, one or more subsets of qEEG data can be further processed. In this embodiment, qEEG data from each included paired electrode sites (for example, F3 and F4, and CZ as a reference) can be transformed to the frequency domain on an epoch-by-epoch basis using a Fast Fourier Transform (FFT) in blocks 108 and 110 for each respective epoch. For each frequency interval (defined by the frequency resolution of the data), using the data from all the transformed epochs, the technique can take the overall maximum and overall minimum of the calculated power values. As shown in this embodiment, each set of data from the transformed epochs can be used to create one or more spectral patterns. In other embodiments, fewer or greater numbers of data sets can be processed using FFT or other techniques to create one or more spectral patterns.

Blocks 108 and 110 are followed by block 112, in which based in part on at least the qEEG data, spectral patterns are created. A spectral pattern can be defined as the region contained between a set of maximum and minimum power points, and can be described by feature vectors, one for each frequency interval, defined for instance, by frequency interval, maximum power, and minimum power. The information preceding the frequency interval can include the patient, trial number, and any additional information desired for the data analysis. The methods for data analysis using spectral patterns can be derived from mathematical set theory, and some or all applications and subsequent equations can be defined in related terms.

Furthermore, in this embodiment, when two or more spectral patterns have been obtained for a single subject or patient, the static and dynamic portions of the spectral patterns can be separated, for instance, using the feature vectors and mathematical set theoretical methods. Each of the spectral patterns from the particular patient can be denoted as p(i), where i is an indexing variable for the patterns, numbering from 1 to n, and where n is the total number of spectral patterns for the patient. The static component of the spectral pattern can then be defined as the intersection of all the obtained spectral patterns, that is, the area defined by the least of the maximum power values and the greatest of the minimum power values over all p(i) at each frequency interval. In set theoretical notation, this definition is equivalent to $$s = \bigcap_i p(i)$$

where s denotes the static component of the EEG data, which is in itself a spectral pattern. The dynamic component of each spectral pattern p(i) can be defined as the difference between that spectral pattern and the static component defined above. Once again, using set-theoretical notation, this is equivalent to $d_i=p(i)-s$ where $d_i$ denotes the dynamic component of the $i^{th}$ spectral pattern, p(i) as before denotes the $i^{th}$ spectral pattern, and s denotes the static component as defined above. The static and dynamic components can be treated as individual spectral patterns for the purposes of measuring asymmetry and other types of analysis. In some embodiments, this particular method can distinguish between state and trait phenomena in qEEG data.

Block 110 is followed by decision block 112, in which a determination is made whether another trial or test is available or possible. That is, whether additional qEEG data can be collected from the patient or subject and processed as needed. If another trial or test is available or possible, the YES branch can be followed to block 102 and blocks 102-110 can be repeated. Therefore, as needed, additional qEEG data can be collected from the patient or subject. In one embodiment, two or more visits spaced several days or weeks apart can be performed for a repeated measures analysis of qEEG data for the subject with the subject's eyes closed. In this instance, the split between the qEEG static and dynamic components can be more precise and more easily distinguishable. In some embodiments, if the subject has a menstrual cycle, qEEG data collection during the luteal phase can be avoided.

Returning to decision block 112, if a determination is made that there is not another trial or test available or possible, the NO branch is followed to block 114. At block 114, the EEG components comprising the qEEG data can be separated and analyzed. In this embodiment, using the spectral patterns from each site as described above, the spectral patterns can be separated into static and dynamic components. For example, qEEG data or measurements can be separated into a baseline set of information with acute qEEG features superimposed over the top of the baseline, in other words, the qEEG data can be separated between static (baseline) and dynamic (superimposed) components.

As shown in this embodiment, the static and dynamic asymmetry between the patterns can be measured or otherwise determined. For measuring the static asymmetry, the branch labeled "STATIC" can be followed from block 114 to blocks 116 and 118. For measuring the dynamic asymmetry, the branch labeled "DYNAMIC" can be followed from block 114 to blocks 120 and 122.

Figure 7:
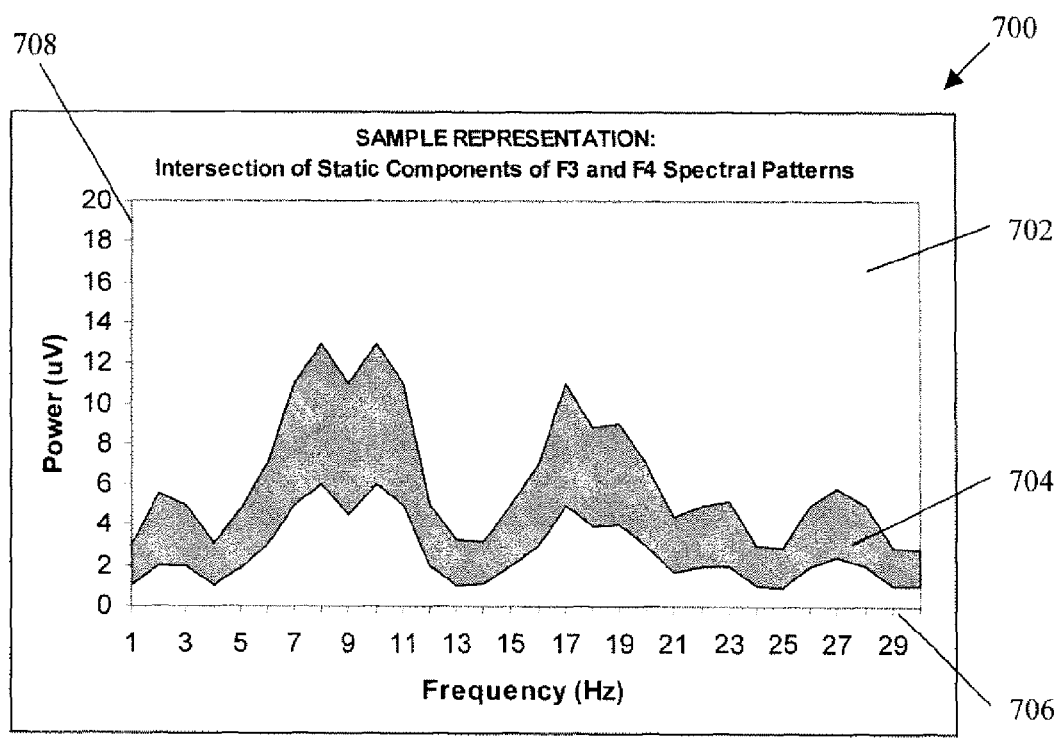
FIG. 7 is an example representation of a report including data analysis results obtained with an embodiment of the invention.

In blocks 116 and 120, the static asymmetry and dynamic asymmetry are calculated or otherwise determined, respectively. For example, for each spectral pattern (noting again that the static and dynamic components are interpreted as separate spectral patterns for this example method) the spectral pattern technique described above can measure or otherwise determine asymmetry by intersecting the left and right spectral patterns, and the intersection can be removed from each original pattern for analysis of the data. In FIG. 7, 700 provides a sample representation of the intersection of right (F4) and left (F3) static components of spectral patterns. Using set theory notation, asymmetry can be defined as P'(L) =P(L)−P(L)∩P(R), where P'(L) denotes the asymmetry pattern of the left side, and P(L) and P(R) denote the left and right spectral patterns, respectively. The same equation with the L and R's reversed can define asymmetry for the right side. These two results, which once again are spectral patterns themselves, are then compared in the alpha frequency band, for instance, the 8-13 Hz range, to measure or otherwise determine the asymmetry.

The spectral pattern technique can allow for a similarity comparison between two or more spectral patterns, for example from different times and sites from a single individual, or between two individuals within a group. The similarity coefficient can once again be calculated using set-theoretical techniques, the notation of which is used herein. Denoting the two patterns m and n, we define the similarity between the patterns as $$s'(m, n) = \frac{|m \cap n|}{|m \cup n|},$$

or the ratio of the intersection of the two patterns to the union of the two patterns on a vector-by-vector basis. In other words, this is the ratio of the number of area elements the two patterns share to the total number contained in the two. Overall similarity can then be defined as $$s(m, n) = \sum_k w(k) s'_k(m, n)$$

where the w(k) is a weighting factor for the $k^{th}$ frequency band subject to the condition that w(k) sums to 1 over all included k values. Initially, w(k) is proportional to 1/k, but a learning optimization algorithm or other similar techniques can adjust this initial weighting. Note the subscript k denotes the restricting of the similarity s' to the $k^{th}$ frequency band, all bands being weighted and then summed together to determine the overall similarity coefficient for the patterns being analyzed.

Using the above calculations for spectral components of paired right and left side electrodes, a respective power for each frontal region can be calculated. The powers can be calculated from each of the static and dynamic feature vectors using the average of the maximum and minimum powers, and then applied to the standard asymmetry equation (R−L)/(R+L), where R equals right side electrode power and L equals left side electrode power. Note that similar equations of asymmetry can be applied to this technique and that amplitude or power values may be used. In order to conform to convention from previous studies, the alpha band can be defined as the 8-13 Hz range of the transformed data. Note that the alpha range has not been standardized by the healthcare field and a variety of ranges may be used to similar effect.

Epoch by epoch power values of paired right and left side electrodes can be used to calculate asymmetry for each epoch in the alpha range (8-13 Hz). This set of individual asymmetry values can be used to calculate a further spectral pattern for asymmetry, as described above, producing feature vectors for the static and dynamic components of asymmetry. The maximum and minimum values of the feature vectors can be averaged to produce static and dynamic asymmetry results. In addition, epoch by epoch asymmetry values can be separated into two sets defined by the ranges of the static and dynamic feature vectors. The percentage time is the percentage of the total time in which asymmetry is calculated (on an epoch-by-epoch basis) to be greater than zero, which is calculated for both the static and dynamic sets of asymmetry values.

In summary, asymmetry in qEEG data can be calculated using some or all of the following techniques:
1) Spectral asymmetry can be calculated by removing the intersection of the left and right (F3 and F4) spectral patterns from each of the original patterns. Analysis of the similarity of the patterns can be calculated using a ratio of the intersection of the sets and the union of the sets.
2) Feature vectors can be used in the derivation of the standard frontal power and EEG asymmetry values of the static and the dynamic components in the alpha frequency band.
3) Percent time of left and right favored asymmetry can be calculated treating the static and dynamic components of the spectral patterns as individual spectral patterns.

In addition, embodiments of the invention can determine some or all of the following indicator variables associated with qEEG data:
1) "Static spectral asymmetry" by intersection of right and left side static components.
2) "Dynamic spectral asymmetry" by intersection of right and left side dynamic components.
3) "Static power" by average of the maximum and minimum powers of the right or left side static components.
4) "Dynamic power" by average of the maximum and minimum powers of the right or left side dynamic components.
5) Static spectral asymmetry by average of the maximum and minimum powers of the right and left side static components applied to (R−L)/(R+L).

6) Dynamic spectral asymmetry by average of the maximum and minimum powers of the right and left side dynamic components applied to (R−L)/(R+L).
7) Static spectral asymmetry by spectral pattern analysis of asymmetry calculated by (R−L)/(R+L).
8) Dynamic spectral asymmetry by spectral pattern analysis of asymmetry calculated by (R−L)/(R+L).
9) Percent time of left and/or right favored asymmetry by ratio of epochs with asymmetry (R−L)/(R+L) greater than zero.
10) "Static percent time" of left and/or right favored asymmetry by ratio of static epochs with asymmetry (R−L)/(R+L) greater than zero.
11) "Dynamic percent time" of left and/or right favored asymmetry by ratio of dynamic epochs with asymmetry (R−L)/(R+L) greater than zero.

Blocks 116 and 120 are followed by blocks 118 and 122, respectively. In block 118, a determination of a risk for a disorder, such as depression, can be made. That is, based on the static spectral asymmetry for a particular set of qEEG data associated with a patient or subject, a risk that the patient or subject has a particular disorder can be determined. For example, static spectral asymmetry in a particular set of qEEG data and at least one indicator variable can be analyzed. In other embodiments, any combination of the above indicator variables or other qEEG data-related variables can be analyzed. In other embodiments, any combination of the above indicator variables or other qEEG data-related variables or other clinical data can be analyzed. In any event, asymmetry values derived from static components of qEEG data can be applied to assessment of an individual with depression or other related emotional psychopathology, for instance, determining whether a particular individual is at risk for depression.

In block 122, a particular disorder and associated treatment can be tracked based in part on at least the dynamic spectral asymmetry for a particular set of qEEG data associated with a patient or subject. For example, the asymmetry values derived from dynamic components of qEEG data can be applied to the tracking of changes in symptomology of an individual over time in the presence and absence of treatment, for instance, tracking depression in a particular individual and predicting, evaluating, and determining the effects of any treatment.

Thus, in one embodiment as shown in block 118, the static asymmetry values can be compared with one or more previously stored values or other data in one or more databases and/or cutoffs derived from clinical research which can associate the asymmetry values with baseline presence or statistical risk of depression. In another embodiment as shown in block 122, the dynamic asymmetry values can be compared with one or more previously stored values or other data in one or more databases and/or cutoffs derived from clinical research which can track normalization of dynamic asymmetry concurrent with the attenuation of depressive symptoms with treatment or therapy.

Blocks 120 and 124 are followed by block 126, in which the method 100 ends. Other example methods can include fewer or greater numbers of elements or steps in accordance with other embodiments of the invention.

Figure 2:
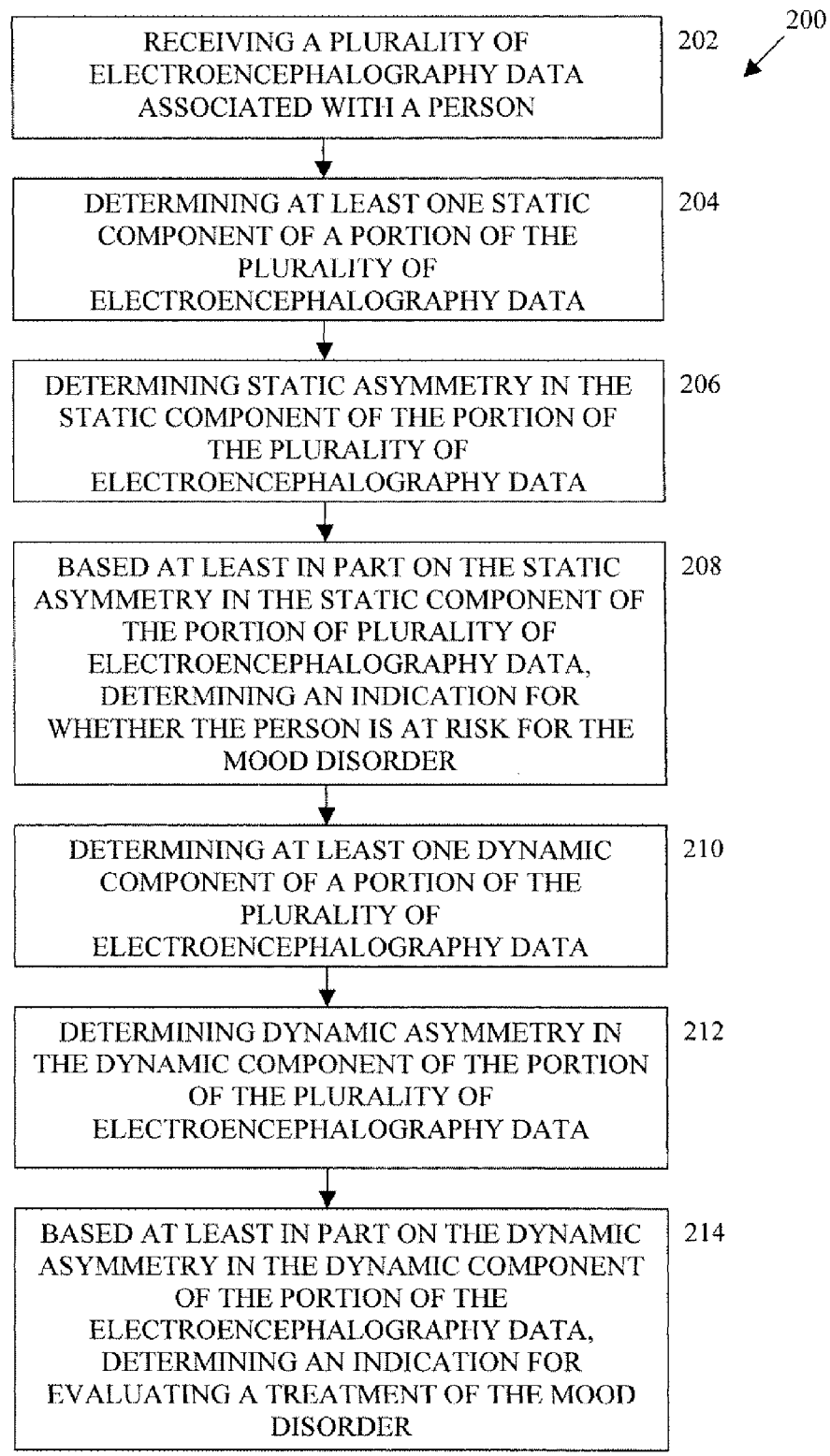
FIG. 2 is a flowchart for another example method in accordance with an embodiment of the invention.

Another example of a method for analyzing and assessing depression and other mood disorders in an individual using electroencephalography or qEEG measurements according to an embodiment of the invention is shown in FIG. 2. The method 200 shown can be implemented with a system such as 602 in FIG. 6. The example method 200 begins at block 202.

In block 202, a plurality of electroencephalography data associated with a person is received. For example, qEEG data can be received from a patient, such as 614 in FIG. 6, via a client device, such as 618 in FIG. 6, or a biological data collector, such as 628 in FIG. 6. Other embodiments of the invention can collect electroencephalography data associated with a person as described above in FIG. 1.

Block 202 is followed by block 204, in which at least one static component associated with a portion of the plurality of electroencephalography data is determined. For example, a static component of at least some of the qEEG data can be determined by a report generation module such as 608 in FIG. 6, a processor such as 638 in FIG. 6, or other processing component associated with the system 602 of FIG. 6. Other embodiments of the invention can determine at least one static component associated with electroencephalography data as described above in FIG. 1.

Block 204 is followed by block 206, in which static asymmetry in the static component of the portion of the plurality of electroencephalography data is determined. For example, static asymmetry can be determined by a report generation module such as 608 in FIG. 6, a processor such as 638 in FIG. 6, or other processing component associated with the system 602 of FIG. 6. Other embodiments of the invention can determine static asymmetry of electroencephalography data as described above in FIG. 1.

Block 206 is followed by block 208, in which based at least in part on the static asymmetry of the portion of plurality of electroencephalography data, an indication for whether the person is at risk for a mood disorder is determined. For example, an indication can be determined by a report generation module such as 608 in FIG. 6, a processor such as 638 in FIG. 6, or other processing component associated with the system 602 of FIG. 6. By way of further example, depending on how static asymmetry is determined for a particular person, various aspects of the static asymmetry can be utilized to characterize a degree, likelihood, or risk that the particular person has for at least one mood disorder, such as depression. Other embodiments of the invention can determine an amount of risk based on the static asymmetry as described above in FIG. 1.

Block 208 is followed by block 210, in which at least one dynamic component of a portion of the plurality of electroencephalographic data is determined. For example, a dynamic component associated with at least some of the qEEG data can be determined by a report generation module such as 608 in FIG. 6, a processor such as 638 in FIG. 6, or other processing component associated with the system 602 of FIG. 6. Other embodiments of the invention can determine at least one dynamic component associated with electroencephalography data as described above in FIG. 1.

Block 210 is followed by block 212, in which dynamic asymmetry in the dynamic component of the portion of plurality of electroencephalography data is determined. For example, dynamic asymmetry can be determined by a report generation module such as 608 in FIG. 6, a processor such as 638 in FIG. 6, or other processing component associated with the system 602 of FIG. 6. Other embodiments of the invention can determine dynamic asymmetry of electroencephalography data as described above in FIG. 1.

Block 212 is followed by block 214, in which based at least in part on the dynamic asymmetry in the dynamic component of the portion of the electroencephalography data, an indication for evaluating a treatment of the mood disorder is determined. For example, an indication can be determined by a report generation module such as 608 in FIG. 6, a processor such as 638 in FIG. 6, or other processing component associated with the system 602 of FIG. 6. By way of further example, depending on how dynamic asymmetry is determined for a particular person, various aspects of the dynamic asymmetry can be utilized to characterize the particular treatment of a mood disorder, such as depression, of interest. Other embodiments of the invention can determine an amount of risk based on the static asymmetry as described above in FIG. 1.

The method 200 ends at block 214. Other embodiments of methods in accordance with the invention can have fewer or greater numbers of elements or steps. In addition, other embodiments can include other elements or steps in conjunction with the elements or steps of method 200.

Figure 3:
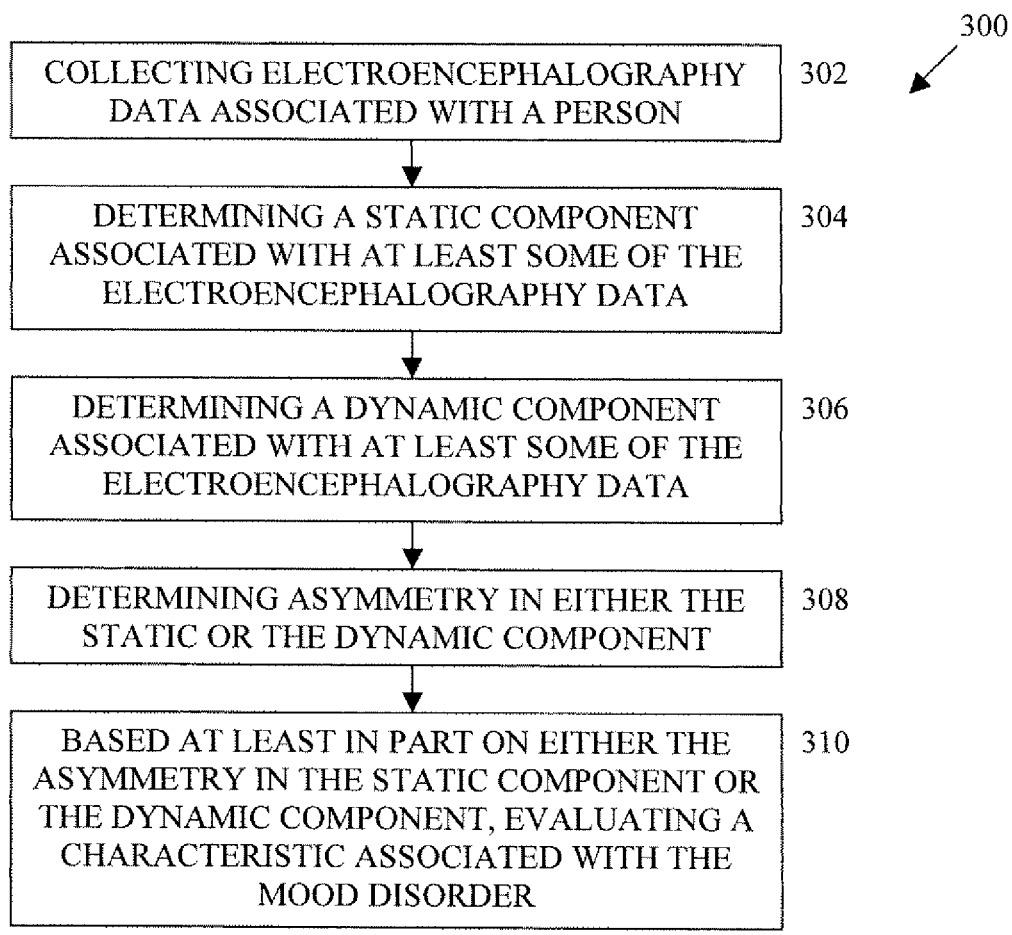
FIG. 3 is a flowchart for another example method in accordance with an embodiment of the invention.

Another example of a method for analyzing and assessing depression and other mood disorders in an individual using electroencephalography or qEEG measurements according to an embodiment of the invention is shown in FIG. 3. The method 300 shown can be implemented with a system such as 602 in FIG. 6. The example method 300 begins at block 302.

In block 302, electroencephalography data associated with a person is collected. For example, qEEG data can be collected from a patient, such as 614 in FIG. 6, via a client device, such as 618 in FIG. 6, or a biological data collector, such as 628 in FIG. 6. Other embodiments of the invention can collect electroencephalography data associated with a person as described above in FIG. 1.

Block 302 is followed by block 304, in which a static component associated with at least some of the electroencephalography data is determined. For example, a static component of at least some of the qEEG data can be determined by a report generation module such as 608 in FIG. 6, a processor such as 638 in FIG. 6, or other processing component associated with the system 602 of FIG. 6. Other embodiments of the invention can determine at least one static component associated with electroencephalography data as described above in FIG. 1.

Block 304 is followed by block 306, in which a dynamic component associated with at least some of the electroencephalographic data is determined. For example, a dynamic component associated with at least some of the qEEG data can be determined by a report generation module such as 608 in FIG. 6, a processor such as 638 in FIG. 6, or other processing component associated with the system 602 of FIG. 6. Other embodiments of the invention can determine at least one dynamic component associated with electroencephalography data as described above in FIG. 1.

Block 306 is followed by block 308, in which asymmetry in either the static or dynamic component is determined. For example, static or dynamic asymmetry can be determined by a report generation module such as 608 in FIG. 6, a processor such as 638 in FIG. 6, or other processing component associated with the system 602 of FIG. 6. Other embodiments of the invention can determine static or dynamic asymmetry of electroencephalography data as described above in FIG. 1.

Block 308 is followed by block 310, in which based at least in part in the asymmetry of either the static component or dynamic component, a characteristic associated with a mood disorder is evaluated. For example, asymmetry can be analyzed and a characteristic associated with a mood disorder can be evaluated by a report generation module such as 608 in FIG. 6, a processor such as 638 in FIG. 6, or other processing component associated with the system 602 of FIG. 6. In some embodiments of the invention, a characteristic can be an indicator or indicator variable associated with a mood disorder, such as depression. In other embodiments of the invention, a characteristic can be an indication of whether a particular person is at risk for a mood disorder, such as depression. In other embodiments of the invention, a characteristic can be an indication of or characterization of a particular treatment of a mood disorder, such as depression.

The method 300 ends at block 310. Other embodiments of methods in accordance with the invention can have fewer or greater numbers of elements or steps. In addition, other embodiments can include other elements or steps in conjunction with the elements or steps of method 300.

Figure 4:
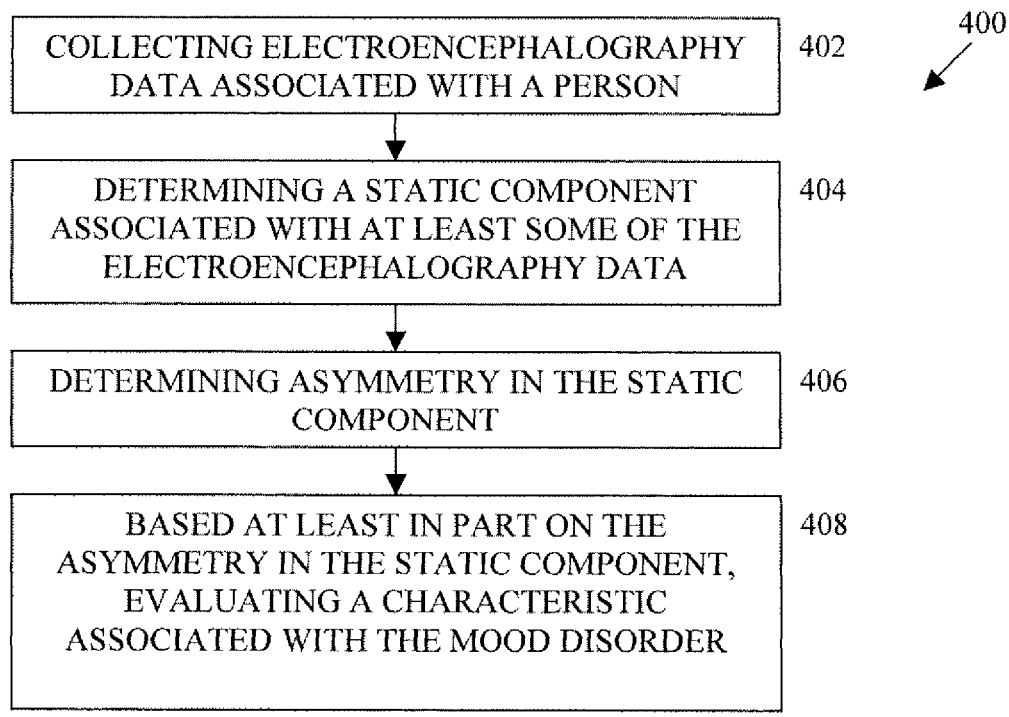
FIG. 4 is a flowchart for another example method in accordance with an embodiment of the invention.

Another example of a method for analyzing and assessing depression and other mood disorders in an individual using electroencephalography or qEEG measurements according to an embodiment of the invention is shown in FIG. 4. The method 400 shown can be implemented with a system such as 602 in FIG. 6. The example method 400 begins at block 402.

In block 402, electroencephalography data associated with a person is collected. For example, qEEG data can be collected from a patient, such as 614 in FIG. 6, via a client device, such as 618 in FIG. 6, or a biological data collector, such as 628 in FIG. 6. Other embodiments of the invention can collect electroencephalography data associated with a person as described above in FIG. 1.

Block 402 is followed by block 404, in which a static component associated with at least some of the electroencephalography data is determined. For example, a static component of at least some of the qEEG data can be determined by a report generation module such as 608 in FIG. 6, a processor such as 638 in FIG. 6, or other processing component associated with the system 602 of FIG. 6. Other embodiments of the invention can determine at least one static component associated with electroencephalography data as described above in FIG. 1.

Block 404 is followed by block 406, in which asymmetry in the static component is determined. For example, static asymmetry can be determined by a report generation module such as 608 in FIG. 6, a processor such as 638 in FIG. 6, or other processing component associated with the system 602 of FIG. 6. Other embodiments of the invention can determine static asymmetry of electroencephalography data as described above in FIG. 1.

Block 406 is followed by block 408, in which based at least in part in the asymmetry of the static component, a characteristic associated with a mood disorder is evaluated. For example, asymmetry can be analyzed and a characteristic associated with a mood disorder can be evaluated by a report generation module such as 608 in FIG. 6, a processor such as 638 in FIG. 6, or other processing component associated with the system 602 of FIG. 6. In some embodiments of the invention, a characteristic can be an indicator or indicator variable associated with a mood disorder, such as depression. In other embodiments of the invention, a characteristic can be an indication of whether a particular person is at risk for a mood disorder, such as depression.

The method 400 ends at block 408. Other embodiments of methods in accordance with the invention can have fewer or greater numbers of elements or steps. In addition, other embodiments can include other elements or steps in conjunction with the elements or steps of method 400.

Figure 5:
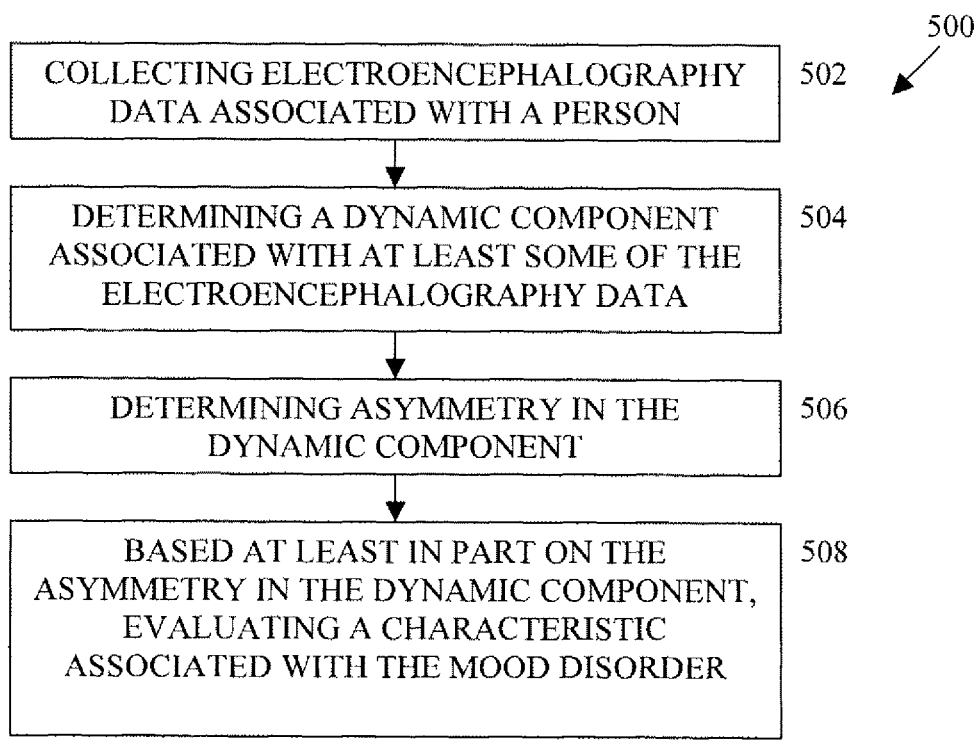
FIG. 5 is a flowchart for another example method in accordance with an embodiment of the invention.

Another example of a method for analyzing and assessing depression and other mood disorders in an individual using electroencephalography or gEEG measurements according to an embodiment of the invention is shown in FIG. 5. The method 500 shown can be implemented with a system such as 602 in FIG. 6. The example method 500 begins at block 502.

In block 502, electroencephalography data associated with a person is collected. For example, qEEG data can be collected from a patient, such as 614 in FIG. 6, via a client device, such as 618 in FIG. 6, or a biological data collector, such as 628 in FIG. 6. Other embodiments of the invention can collect electroencephalography data associated with a person as described above in FIG. 1.

Block 502 is followed by block 504, in which a dynamic component associated with at least some of the electroencephalographic data is determined. For example, a dynamic component associated with at least some of the qEEG data can be determined by a report generation module such as 608 in FIG. 6, a processor such as 638 in FIG. 6, or other processing component associated with the system 602 of FIG. 6. Other embodiments of the invention can determine at least one dynamic component associated with electroencephalography data as described above in FIG. 1.

Block 504 is followed by block 506, in which asymmetry in the dynamic component is determined. For example, dynamic asymmetry can be determined by a report generation module such as 608 in FIG. 6, a processor such as 638 in FIG. 6, or other processing component associated with the system 602 of FIG. 6. Other embodiments of the invention can determine dynamic asymmetry of electroencephalography data as described above in FIG. 1.

Block 506 is followed by block 508, in which based at least in part in the asymmetry of the dynamic component, a characteristic associated with treatment of a mood disorder is evaluated. For example, asymmetry can be analyzed and a characteristic associated with a mood disorder can be evaluated by a report generation module such as 608 in FIG. 6, a processor such as 638 in FIG. 6, or other processing component associated with the system 602 of FIG. 6. In some embodiments of the invention, a characteristic can be an indicator or indicator variable associated with a mood disorder, such as depression. In other embodiments of the invention, a characteristic can be an indication of or characterization of a particular treatment of a mood disorder, such as depression.

The method 500 ends at block 508. Other embodiments of methods in accordance with the invention can have fewer or greater numbers of elements or steps. In addition, other embodiments can include other elements or steps in conjunction with the elements or steps of method 500.

The methods disclosed herein are by way of example only, and other methods in accordance with embodiments of the invention can include other steps, or fewer or greater numbers of steps than the methods herein.

Figure 6:
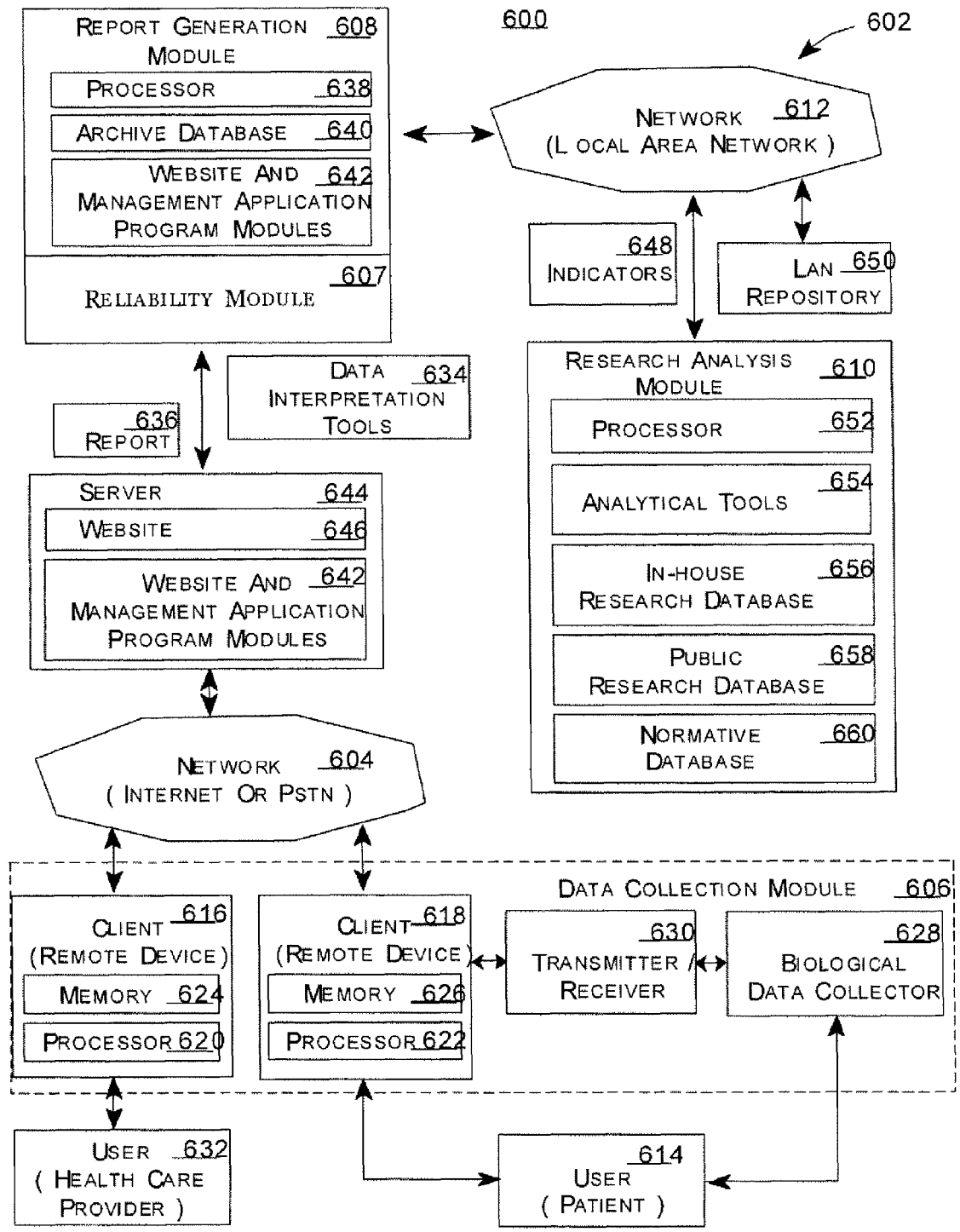
FIG. 6 is an example system in accordance with an embodiment of the invention.

An example system in accordance with an embodiment of the invention is shown as 602 in FIG. 6. FIG. 6 illustrates an example environment 600 for a system 602 in accordance with various embodiments of the invention. Using a system 602 illustrated in FIG. 6, some or all of the methods of FIGS. 1-5 can be implemented.

The environment 600 shown includes a network 604 in communication with the system 602. In turn, the system 602 includes one or more system modules 606, 607, 608, 610 that can operate with and in accordance with embodiments of the invention. Each of the system modules 606, 607, 608, 610 can communicate with each other through the network 604 or via an associated network 612 such as a local area network (LAN). For example, the system modules can be a data collection module 606, a frequency spectrum/reliability module 607, a report generation module 608, and a research analysis module 610. The data collection module 606 and frequency spectrum/reliability module 607 can communicate with the report generation module 608 via the Internet or a network such as 604, and the research analysis module 610 can communicate with the report generation module 608 via a LAN, such as 612. Other system modules in various configurations operating in accordance with embodiments of the invention may exist. The configuration and arrangement of the system modules 606, 607, 608, 610 are shown by way of example only, and other configurations and arrangements of system modules can exist in accordance with other embodiments of the invention.

Each of the system modules 606, 607, 608, 610 can be hosted by one or more processor-based platforms such as those implemented by Windows 98, Windows NT/2000, LINUX-based and/or UNIX-based operating platforms. Furthermore, each of the system modules 606, 607, 608, 610 can utilize one or more conventional programming languages such as DB/C, C, C++, UNIX Shell, and Structured Query Language (SQL) to accomplish various methods, routines, subroutines, and computer-executable instructions in accordance with the invention, including system functionality, data processing, and communications between functional components. Each of the system modules 606, 607, 608, 610 and their respective functions are described in turn below.

The data collection module 606 is adapted to collect biological data from a user such as a patient 614, person, or individual. For example, biological data can include electroencephalography or qEEG data from a patient, such as 614. The data collection module 606 includes one or more clients 616, 618 and/or remote devices in communication with the network 604 such as the Internet. Typically, each client 616, 618 is a processor-based platform such as a personal computer, personal digital assistant (FDA), tablet, or other stationary or mobile computing-type device adapted to communicate with the network 604. Each client 616, 618 can include a respective processor 620, 622, memory 624, 626 or data storage device, biological data collector 628, and transmitter/receiver 630. Other components can be utilized with the data collection module 606 in accordance with other embodiments of the invention.

The biological data collector 628 communicates with at least one client 616, 618 via a transmitter/receiver 630. In the embodiment shown, a biological data collector 628 such as a medical device obtains or otherwise receives biological data in real-time from a user such as a patient 614. The transmitter/receiver 630 transmits the received biological data from the biological data collector 628 or medical device to the client 618. In turn, the client 618 may temporarily store the biological data in memory 626 or otherwise process the data with the processor 622, and further transmit the data via the network 604 to the reliability module 607 and/or report generation module 608. In other embodiments, a biological data collector 628 may locally store and process collected data, and communicate the data directly to the reliability module 607 and/or report generation module 608 via the network 604.

For example, a biological data collector 628 can be a medical device such as a Lexicor Digital Cortical Scan quantitative electroencephalographic (QEEG) data acquisition unit and Electrocap (collectively referred to as "DCS device") provided by Lexicor Medical Technology, Inc. This type of medical device and associated configuration can be connected to a user or patient's head, and when activated, the medical device provides digitized EEG data via a proprietary digital interface and associated software that permits data to be stored locally in a file format such as a Lexicor file format on a host platform. In alternative embodiments, data can be transmitted in real-time via other interfaces such as USB to the host platform such as a server. Stored EEG data can be uploaded to an associated server or client as needed. In other instances, collected or stored data can be burned onto or otherwise stored in a digital format such as a CD-R disk and then transmitted or transferred to an associated server or client.

Note that a Lexicor file format can be a Lexicor raw EEG data file format developed by Lexicor Medical Technology, Inc. This particular file format has a data structure that is adapted to store 24 channels of digitized EEG data to facilitate offline data analysis. Although various EEG storage formats exist, the Lexicor file format can be adapted to handle these and other data storage formats. For example, the Lexicor file format has a global header with 64 integers to handle information such as sample rate, gain of the front end DCS amplifiers, software revision, an total number of epochs. Further, the Lexicor file format can include one or more epochs or sections of raw data including a 256 byte text array to handle comment entries, as well as an array to handle raw digitized EEG data collected by a DCS device during a particular acquisition period for a particular epoch, and a local header containing the epoch number and status of the particular epoch.

A biological data collector 628 can also include, but is not limited to, blood pressure monitors, weight scales, glucose meters, oximeters, spirometers, coagulation meters, urinalysis devices, hemoglobin devices, thermometers, capnometers, electrocardiograms (EKGs), electroencephalagrams (EEGs), other digital medical devices that can output data via a RS-232 port or similar type connection, and other devices or methods that provide data associated with a biological or physiological function. Biological data collected or otherwise received from a user, patient, or individual can include, but is not limited to, blood pressure, weight, blood component measurements, bodily fluid component measurements, temperature, heart measurements, brainwave measurements, and other measurements associated with a biological or physiological function.

The transmitter/receiver 630 typically facilitates the transfer of data between the biological data collector 628 and client 618. The transmitter/receiver 630 can be a stand alone or built-in device. The transmitter/receiver 630 can include, but is not limited to, a RS-232 compatible device, a wireless communication device, a wired communications device, or any other device or method adapted to communicate biological data.

A user such as a healthcare provider 632 can share or separately utilize a client 616, 618 to interact or communicate with the network 604 depending upon the proximity of the client 616, 618 to the patient 614. The healthcare provider 632 and/or patient 614 may receive specific instructions from the report generation module 608 via the same or a respective client 616, 618. For example, in response to a particular condition, the report generation module 608 may request that from the health care provider 632 that specific biological data be collected from the patient 614. Appropriate instructions may be communicated to the health care provider 632 via the network 604 to the client 616. The health care provider 632 can then instruct the patient 614 or otherwise assist the patient 614 in connecting the biological data collector 628 or medical device to the patient 614. When activated, the biological data collector 628 or medical device can transmit biological data associated with the patient 614 via the network 604 or Internet to the report generation module 608. As needed, a healthcare provider 632, and/or patient 614, or other user can input demographic data or otherwise provide demographic data via a respective client 616, 618.

The frequency spectrum/reliability module 607 can be adapted to receive biological data from the data collection module 606, and to process some or all of the biological data to determine one or more reliability indexes based in part on at least some or all of the biological data. In the embodiment shown, a frequency spectrum/reliability module 607 can be a set of computer-executable instructions such as a software program stored on a server such as 644, or another processor-based platform such as a client device in communication with a server. The frequency spectrum/reliability module 607 shown can be integrated with the report generation module 608. In another embodiment, a frequency spectrum/reliability module 607 can be a separate stand alone module with an associated processor such as an apparatus or reliability device. In another embodiment, a frequency spectrum/reliability module 607 can be an incorporated sub-system module for an associated website and management administration program module, such as 642. As needed, various reports can be generated by a frequency spectrum/reliability module 607, and provided to a user, such as a health care provider 632.

The report generation module 608 is adapted to receive, store, and process the biological data from the patient 614 for subsequent retrieval and analysis. The report generation module 608 is also adapted to generate one or more data interpretation tools 634 based upon collected or otherwise received biological data from the patient 614. Further, the report generation module 608 is adapted to generate a report 636 including one or more data interpretation tools to assist a user such as a health care provider 632 in managing and analyzing biological data. An example data interpretation tool and report are described in greater detail with respect to FIG. 7. In addition, the report generation module 608 is adapted to operate in conjunction with or otherwise execute an associated website and management application program module 642.

Typically, the report generation module 608 is a processor-based platform such as a server, mainframe computer, personal computer, personal digital assistant (PDA). The report generation module 608 includes a processor 638, an archive database 640, and a website and management application program module 642. A separate server 644 to host an Internet website 646 can be connected between the report generation module 608 and the network 604 or Internet; or otherwise be in communication with the report generation module 608 and data collection module 606 via the network 604 or Internet. Generally, the separate server 644 is a processor-based platform such as a server or computer that can execute a website and management application program module 642. In any instance, the report generation module 608 communicates with the data collection module 606 via the network 604 or Internet. Other components can be utilized with the report generation module 608 in accordance with other embodiments of the invention.

In one embodiment, the report generation module 608 and other modules, such as 606, 607, 610, 642, can include a set of computer-executable instructions or an associated computer program. The various sets of computer-executable instructions or computer programs can be processed by one or more associated processors, such as 638, or other computer hardware. Those skilled in the art will recognize the various embodiments for such modules and the implementation of these modules in accordance with the invention.

The processor 638 can handle biological data and/or demographic data received from the data collection module 606, or received via the frequency spectrum/reliability module 607. The processor 638 and/or the frequency spectrum/reliability module 607 can store the biological data and demographic data in the archive database 640 for subsequent retrieval, and/or process the biological data using other data received from the research analysis module 610. Typically, the processor 638 and/or the frequency spectrum/reliability module 607 can analyze biological data and/or demographic data from the data collection module 606 and can remove unwanted artifacts from the data. Relevant biological data and/or demographic data can be stored in the archive database 640 or other data storage device until needed. Using one or more indicators 648 received from the research analysis module 610 or otherwise generated or stored by the system 602, the processor 638 can process the biological data and/or demographic data to generate one or more data interpretation tools 634. The processor 638 can generate a report 636 including one or more indicators 638 and associated data interpretation tools 634 for transmission via the network 604 to a user such as the health care provider 632 and/or patient 614.

Data interpretation tools 634 can add relevant information and context to biological and/or demographic data in a report 636, such that the data can be more readily interpreted by a user such as a health care provider 632 to determine the state of a particular condition with a particular patient 614. Data interpretation tools 634 typically include patterns of biological and/or demographic data for normal subjects and subjects with the condition. The patterns of biological and/or demographic data can be presented in a report 636 which can include graphs and text. These patterns are determined from a meta-analysis of the body of scientific literature, and analysis of relevant databases for normal subjects as well as those with a particular condition and those with related conditions.

In one embodiment, biological data such as electroencephalography data or qEEG data can be received or collected by the data collection module 606. The data collection module 606 transmits the data to the report generation module 608, and the report generation module can process the data. For example, a static and a dynamic component of the electroencephalography data can be determined, and static and dynamic asymmetry in the electroencephalography data can also be determined. Various indicators, characteristics, aspects, and qualities associated with the components and asymmetry can be further determined by the report generation module 608. In one embodiment, one or more indicators can be provided by or otherwise obtained from the research analysis module 610, or other components of the system 602. Methods and algorithms for determining components, asymmetry, indicators, characteristics, aspects, and qualities in accordance with embodiments of the invention are disclosed herein with respect to FIGS. 1-5. Using the processed data, the report generation module 608 can further generate an output, such as a report shown and described as 700 with respect to FIG. 7.

The archive database 640 can be a database, memory, or similar type of data storage device. The archive database 640 is adapted to store biological data such as medical images, medical data and measurements, and similar types of information, as well as demographic data as previously described. Generally, the archive database 640 can be utilized by the report generation module 608 to store biological data and demographic data until called upon.

The website and management application program module 642 is typically a set of computer-executable instructions adapted to provide a website 646 with at least one functional module to handle data communication between the website 646 and at least one user such as a health care provider 632 and/or patient 614. The website and management application program module 642 can be hosted by the report generation module 608, separate server, and/or a storage device in communication with the network 604. A website and management application program module 642 can include, but is not limited to, a main login module, a patient management module, a patient qualification module, a patient assessment module, a patient care plan module, a data analysis module, a filter module, an import/export module, a virtual private network electronic data interchange (VPI EDI) module, a reporting module, an indicator report notification module, an indicator report delivery module, an administrative module, a notification (data filter/smart agent) administration module, a database module, and other similar component or functional modules. Other component modules associated with the website and management application program module 642 can operate in accordance with other embodiments of the invention.

The separate server 644 is adapted to host the website 646 viewable via the Internet with a browser application program. Alternatively, the separate server 644 may host a website and management application program module 642 as well. A website 646 provides communication access for a health care provider 632 and/or patient 614 to the report generation module 608. For example, a report 636 generated by the report generation module 608 may be posted to the website 646 for selective access and viewing via the network 604 or Internet by a user such as a health care provider 632 and/or patient 614 operating the same or a respective client 616, 618 via the network 604. In other instances, a report 636 may be transmitted by the report generation module 608 to a user such as a health care provider 632 and/or patient 614 via an electronic mail message communication, a telecommunications device, messaging system or device, or similar type communication device or method. An example of a report generated in accordance with various embodiments of the invention is illustrated and described in detail below in FIG. 7.

The associated network 612 is typically a local area network (LAN) that provides communications between the report generation module 608 and the research analysis module 610. A LAN repository 650 may be connected or otherwise accessible to the associated network 612 for additional storage of biological data, indicators, or other data collected, generated, or otherwise received by the system 602.

The research analysis module 610 is adapted to obtain and collect relevant research materials and data. Furthermore, the research analysis module 610 is adapted to process relevant research materials and data, and can be further adapted to determine one or more indicators 648 for a particular condition. Moreover, in one embodiment, the research analysis module 610 is adapted to provide indicators 648 to the report generation module 608 in response to a particular patient's condition or collected biological and demographic data. Typically, the research analysis module 610 is a processor-based platform such as a server, mainframe computer, personal computer, or personal digital assistant (PDA). The research analysis module 610 includes a processor 652, analytical tools 654, an in-house research database 656, a public research database 658, and a normative database 660. Other components can be utilized with the research analysis module 610 in accordance with the invention.

The processor 652 handles research and data collected or otherwise received by the research analysis module 610. The processor 652 indexes and/or stores the research or data in an associated database for subsequent retrieval, or processes the research and data using one or more analytical tools 654. One or more indicators 648 can be provided or otherwise derived by or from the analytical tools 654, and the processor 652 can transmit any indicators 648 to the report generation module 608 as needed.

At least one analytical tool 654 is utilized by the research analysis module 610. Typically, an analytical tool 654 is an algorithm that utilizes research and data to determine one or more indicators 648 for a particular condition.

The in-house research database 656 can be a collection of research and articles provided by a particular or third-party vendor. Typically, an entity operating the system 602 can provide its own research and articles for a range of conditions. For example, information available from an in-house research database includes, but is not limited to, electronic databases, scientific and research journals, on-line sources, libraries, standard textbooks and reference books, and on-line and printed statements of committees and boards, and the like.

The public research database 658 can be a collection of research and articles provided by one or more third-parties. Typically, research and articles are available for free or upon payment of a fee from a variety of on-line or otherwise accessible sources. For example, information available from a public research database 3656 includes, but is not limited to, electronic databases, scientific and research journals, on-line sources, libraries, standard textbooks and reference books, on-line and printed statements of committees and boards, and the like.

The normative database 660 can be a collection of electronic databases, scientific and research journals, on-line sources, libraries, standard textbooks and reference books, on-line and printed statements of committees and boards, and the like.

Another example system to collect and analyze qEEG measurements for analyzing and assessing depression in an individual will be implemented by Lexicor Medical Technology, Inc. of Augusta, Ga. Other suitable systems and components to collect qEEG measurements have been disclosed in U.S. Ser. No. 11/053,627, entitled "Associated Systems and Methods For Managing Biological Data and Providing Data Interpretation Tools," filed Feb. 8, 2005, which is a continuation-in-part of U.S. Ser. No. 10/368,295, entitled "Systems and Methods For Managing Biological Data and Providing Data Interpretation Tools," filed Feb. 18, 2003, which claims priority to U.S. Provisional Patent Application No. 60/358,477, filed Feb. 19, 2002, wherein the contents of these applications are incorporated herein by reference. Other system embodiments in various configurations and including other components operating in accordance with the invention may exist.

In one embodiment, a data collection module, such as 606 in FIG. 6, can receive qEEG data as described above in FIGS. 1-6. The data collection module can operate in conjunction with a report generation module, such as 608 in FIG. 6, to process the qEEG data in accordance with some or all of the methods, processes, procedures, and techniques described above. The report generation module 608 can include associated reporting and communication functionality to provide electronic and/or printed report formats to a variety of healthcare professionals, researchers, or other users. In one embodiment, various report formats can be provided via a network, such as the Internet or network 604 in FIG. 6.

FIG. 7 illustrates an example representation of a report including data analysis results obtained using an embodiment of the invention. The report 700 can include data, such as text or a graph 702. In this example, electroencephalography data has been processed by a report generation module, such as 608 in FIG. 6. The report generation module 608 can determine static components of the electroencephalography data. The report generation module 608 can determine the intersection of the spectral patterns for left and right static components of the data. As shown in FIG. 7, the report generation module 608 can generate, output, or otherwise graphically depict or illustrate the intersection of the spectral patterns for left and right (F3 and F4) static components of the data. The intersection of the left and right (F3 and F4) static components is represented by the data 704 shown in the graph 702. The graph 702 includes a plot of frequency in Hertz on the x-axis 706 versus power in μV units on the y-axis 708. The report generation module 608 can plot the data 704 for the intersection of the two static components as shown in the graph 702. Using the intersection of the two sets of data 704, the report generation module 608 can determine a static asymmetry for the electroencephalography data. Based at least in part on the static asymmetry, the report generation module 608 or a user can further evaluate or otherwise determine a risk that the patient or subject has a particular disorder. Based at least in part on the static asymmetry, the report generation module 608 or a user can implement analytical tools 654 such as a learning-type algorithm to define one or more weighting factors to ascertain an indicator 648 such as a patient's similarity and/or risk relative to values in a database 656, 658, 660 of individuals in the presence or absence of a particular disorder or condition.

Other embodiments of a suitable report can include other types of data, text, and graphs. For instance, various indicators, characteristics, aspects, and qualities associated with components, asymmetry, and biological data such as electroencephalography data can be included in a report generated by a report generation module such as 608 in FIG. 6.

While the above description contains many specifics, these specifics should not be construed as limitations on the scope of the invention, but merely as exemplifications of the disclosed embodiments. Those skilled in the art will envision many other possible variations that are within the scope of the invention as defined by the claims appended hereto.

The invention claimed is:

1. A computer operable method for analyzing and assessing a mood disorder in a person, comprising:

receiving, in the computer, electroencephalography data associated with the person, the electroencephalography data including at least one static component corresponding to a baseline level of behavioral functioning of the person and including at least one dynamic component corresponding to an acute level of behavioral expression of the person;

determining, by operation of the computer, the static component of a portion of the electroencephalography data, wherein the static component is independent of the dynamic component included in the electroencephalography data;

determining, by operation of the computer, the dynamic component of the electroencephalography data, wherein the dynamic component is independent of the static component included in the electroencephalography data;

determining, by operation of the computer, a static asymmetry in the static component, wherein the static asymmetry is determined by computing an intersection between a left spectral pattern of the static component and a right spectral pattern of the static component and by removing the intersection from the left and right spectral patterns of the static component; and determining, by operation of the computer, a dynamic asymmetry in the dynamic component, wherein the dynamic asymmetry is determined by computing an intersection between a left spectral pattern of the dynamic component and a right spectral pattern of the dynamic component and by removing the intersection from the left and right spectral patterns of the dynamic component; and based at least in part on the static asymmetry in the static component and the dynamic asymmetry in the dynamic component, determining, by operation of the computer, an indication for whether the person is at risk for the mood disorder, wherein the mood disorder comprises at least one of the following: depression, bipolar disorder, or a disorder with at least one genetic-related component.

2. The method of claim 1, further comprising:

based at least in part on the dynamic asymmetry in the dynamic component, determining, by operation of the computer, an indication for predicting and evaluating a treatment response of the mood disorder, receiving, in the computer, a plurality of data sets associated with the person, wherein the plurality of data sets comprises electroencephalography data for the person collected pre-treatment and comprises electroencephalography data for the person collected post-treatment.

3. A computer operable method for analyzing and assessing a mood disorder in person using electroencephalography data, comprising:

collecting, in the computer, electroencephalography data from the person, the electroencephalography data including at least one static component corresponding to a baseline level of behavioral functioning of the person and including at least one dynamic component corresponding to an acute level of behavioral expression of the person;

determining, by operation of the computer, the static component associated with a portion of the electroencephalography data, wherein the static component is independent of the dynamic component included in the electroencephalography data;

determining, by operation of the computer, the dynamic component of the portion of the electroencephalography data wherein the dynamic component is independent of the static component included in the electroencephalography data;

determining, by operation of the computer, a static asymmetry in the static component and a dynamic asymmetry in the dynamic component, wherein the static asymmetry is determined by computing an intersection between a left spectral pattern of the static component and a right spectral pattern of the static component and by removing the intersection from the left and right spectral patterns of the static component, wherein the dynamic asymmetry is determined by computing an intersection between a left spectral pattern of the dynamic component and a right spectral pattern of the dynamic component and by removing the intersection from the left and right spectral patterns of the dynamic component;

based at least in part on the static asymmetry in the static component and the dynamic asymmetry in the dynamic component, evaluating, by operation of the computer, a characteristic associated with the mood disorder, wherein the characteristic comprises at least one of the following: a risk of having the mood disorder, or a symptom of the mood disorder.

4. A system for analyzing and assessing a mood disorder in a person, comprising:

a data collection module adapted to:
receive electroencephalography data associated with the person, the electroencephalography data including at least one static component corresponding to a baseline level of behavioral functioning of the person and including at least one dynamic component corresponding to an acute level of behavioral expression of the person;

a report generation module adapted to:

determine the static component of a portion of the plurality of data sets, wherein the static component is independent of the dynamic component included in the plurality of data sets;

determine the dynamic component of the portion, wherein the dynamic component is independent of the static component included in the plurality of data sets;

determine static asymmetry in the static component, wherein the static asymmetry is determined by computing an intersection between a left spectral pattern of the static component and a right spectral pattern of the static component and by removing the intersection from the left and right spectral patterns of the static component; and determine dynamic asymmetry in the dynamic component, wherein the dynamic asymmetry is determined by computing an intersection between a left spectral pattern of the dynamic component and a right spectral pattern of the dynamic component and by removing the intersection from the left and right spectral patterns of the dynamic component; and based at least in part on the static asymmetry in the static component and the dynamic asymmetry in the dynamic component, output an indication of whether the person is at risk for the mood disorder, wherein the mood disorder comprises at least one of the following: depression, bipolar disorder, or a disorder with at least one genetic-related component.

5. The system of claim 4, wherein the report generation module is further adapted to:

based at least in part on the dynamic asymmetry in the dynamic component, output an indication of predicting a treatment response of the mood disorder; and based at least in part on the dynamic asymmetry in the dynamic component, output an indication of evaluating a treatment response of the mood disorder, receiving, in the computer, a plurality of data sets associated with the person, wherein the plurality of data sets comprises electroencephalography data for the person collected pre-treatment and comprises electroencephalography data for the person collected post-treatment.

6. A system for analyzing and assessing a mood disorder in a person, comprising:

a data collection module adapted to:
receive electroencephalography data associated with the person, electroencephalography data including at least one static component corresponding to a baseline level of behavioral functioning of the person and including at least one dynamic component corresponding to an acute level of behavioral expression of the person;

a report generation module adapted to:

determine the static component of a portion of the plurality of data sets, wherein the static component is independent of the dynamic component included in the plurality of data sets;

determine the dynamic component of the portion, wherein the dynamic component is independent of the static component included in the plurality of data sets;

determine static asymmetry in the static component, wherein the static asymmetry is determined by computing an intersection between a left spectral pattern of the static component and a right spectral pattern of the static component and by removing the intersection from the left and right spectral patterns of the static component;

determine dynamic asymmetry in the dynamic component, wherein the dynamic asymmetry is determined by computing an intersection between a left spectral pattern of the dynamic component and a right spectral pattern of the dynamic component and by removing the intersection from the left and right spectral patterns of the dynamic component; and based at least in part on the static asymmetry in the static component and the dynamic asymmetry in the dynamic component, output an indication of a characteristic of the mood disorder, wherein the characteristic comprises at least one of the following: a risk of having the mood disorder, or a symptom of the mood disorder.

* * * * *